United States Patent
Schmidt

(10) Patent No.: US 9,389,418 B2
(45) Date of Patent: Jul. 12, 2016

(54) OBJECTIVE FOR A DENTAL CAMERA AND METHOD FOR CREATING AN IMAGE

(75) Inventor: Volker Schmidt, Berlin (DE)

(73) Assignee: SIRONA DENTAL SYSTEMS GmbH, Bensheim (DE)

( * ) Notice: Subject to any disclaimer, the term of this patent is extended or adjusted under 35 U.S.C. 154(b) by 1151 days.

(21) Appl. No.: 13/055,955

(22) PCT Filed: Aug. 3, 2009

(86) PCT No.: PCT/EP2009/059994
§ 371 (c)(1),
(2), (4) Date: May 26, 2011

(87) PCT Pub. No.: WO2010/012839
PCT Pub. Date: Feb. 4, 2010

(65) Prior Publication Data
US 2011/0221879 A1    Sep. 15, 2011

(30) Foreign Application Priority Data
Aug. 1, 2008  (DE) .......................... 10 2008 040 944

(51) Int. Cl.
*A61B 1/04*  (2006.01)
*G02B 27/00*  (2006.01)
(Continued)

(52) U.S. Cl.
CPC ........ *G02B 27/0018* (2013.01); *A61B 1/00188* (2013.01); *A61B 1/0615* (2013.01); *A61B1/0669* (2013.01); *A61B 1/247* (2013.01); *G02B 13/22* (2013.01); *G02B 23/243* (2013.01); *G06T 5/006* (2013.01)

(58) Field of Classification Search
CPC .......... H01J 2237/04928; G02B 13/22; A61B 5/0088
See application file for complete search history.

(56) References Cited

U.S. PATENT DOCUMENTS 4,415,239 A    11/1983  Humphrey .................... 350/433
4,730,910 A  *  3/1988  Humphrey .................... 359/601
(Continued)

FOREIGN PATENT DOCUMENTS

DE    23 40 687 A1    2/1975
DE    31 43 137 C2   10/1985
(Continued)

OTHER PUBLICATIONS

Rogers, et al., "Removal of ghost images by using tilted element optical systems with polynomial surfaces for aberration compensation," Optical Society of America, Optics Letters, vol. 31, No. 4 (2005) 504-06.
(Continued)

*Primary Examiner* — Farzana Hossain
*Assistant Examiner* — Christopher Findley
(74) *Attorney, Agent, or Firm* — Fitzpatrick, Cella, Harper & Scinto

(57) ABSTRACT

The invention relates to an objective (4) and to a method for designing said objective (4) for a dental camera (1), the objective (4) comprising at least two lenses (9, 10, 20, 21) and the dental camera (1) comprising a light source (3) and an image sensor (7). An illuminating beam emitted by the light source (3) is focused by the objective (4), imaged on an object (8) to be measured, and reflected by the object (8) to be measured to form a monitoring beam (12). The monitoring beam (12) passes through the objective (4) and is directed toward the image sensor (7), the illuminating beam (11) being partially reflected by surfaces (9', 9', 9''', 10', 10''', 20', 20''', 21', 21''') of the lenses (9, 10, 20, 21) to form reflected beams (17.1 to 17.8). The objective (4) comprises means (27) for tilting each lens (9, 10, 20, 21) relatively to the illuminating beam (11) such that the optical axis (9'''' 10''', 15.1, 15.2) of each lens (9, 10, 20, 21) forms an angle of tilt ($\alpha, \beta$) with the illuminating beam (11), the size of said angle being such that the reflected beams (17.1 to 17.8) can be reflected in a direction away from the pupil of the monitoring beam (12).

20 Claims, 3 Drawing Sheets

(51) Int. Cl.
  *A61B 1/247* (2006.01)
  *G02B 13/22* (2006.01)
  *G02B 23/24* (2006.01)
  *G06T 5/00* (2006.01)
  *A61B 1/06* (2006.01)
  *A61B 1/00* (2006.01)

(56) References Cited

U.S. PATENT DOCUMENTS

| | | | |
|---|---|---|---|
| 6,285,799 B1 | 9/2001 | Dance et al. | 382/261 |
| 8,270,689 B2 * | 9/2012 | Liang et al. | 382/128 |
| 2008/0174678 A1 | 7/2008 | Solomon | 348/231.99 |

FOREIGN PATENT DOCUMENTS

| | | |
|---|---|---|
| DE | 103 16 416 A1 | 10/2004 |
| DE | 10 2005 043 402 A1 | 3/2007 |
| EP | 0 215 566 A2 | 3/1987 |
| EP | 0 615 721 A1 | 9/1994 |

OTHER PUBLICATIONS

Rogers, "Techniques and tools for obtaining symmetrical performance from tilted-component systems," Society of Photo-Optical Instrumentation Engineers, Optical Engineering, vol. 39, No. 7 (2000) 1776-87.

* cited by examiner

OBJECTIVE FOR A DENTAL CAMERA AND METHOD FOR CREATING AN IMAGE

The present application is a National Stage filing under 35 U.S.C. §371 of International Application No. PCT/EP2009/059994, filed. Aug. 3, 2009, which claims priority to German Patent Application No. 10 2008 040 944.8, filed Aug. 1, 2008. Each prior application is incorporated by reference herein in its entirety, as if set forth fully herein.

The invention relates to an objective for a dental camera and to a method for creating an image by means of such an objective. The objective comprises at least two lenses, and the dental camera comprises a light source and an image sensor, an illuminating beam emerging from the light source is focused by the objective and imaged on an object to be measured and reflected thereby to form a monitoring beam. The monitoring beam passes through the objective and is directed toward the image sensor, the illuminating beam being partially reflected to the image-sensor side by surfaces of any one of the lenses to form a reflected beam.

PRIOR ART

A number of objectives having reduced scattered light are known in the prior art. It is desirable, particularly in the field of photography, to reduce the scattered light occurring at the outer and inner surfaces of the objective as a result of diffuse or specular reflections passing to the image sensor.

Lens hoods reduce the occurrence of scattered light by preventing light from striking the optical system from the side.

Furthermore, surfaces of lenses are coated in order to reduce specular reflections. It is a property, particularly of telecentric optical systems, to focus the light reflected by the field lens onto the optical sensor.

It is an object of this invention to provide an objective, of which the image defects resulting from specular reflections at the surfaces of lenses in the objective are reduced.

SUMMARY OF THE INVENTION

This object is achieved by the present invention.

According to the invention, an objective for a dental camera comprises at least two lenses, the dental camera comprising a light source and an image sensor. An illuminating beam emitted by the light source is focused by the objective and imaged on an object to be measured and reflected by the object to be measured to form a monitoring beam. The monitoring beam passes through the objective and is directed toward the image sensor, the illuminating beam being reflected, in part, by surfaces of the lenses in the form of reflected beams. Means are provided to tilt each of the lenses relatively to the illuminating beam such that the optical axis of each lens forms an angle of tilt with the illuminating beam, which angle of tilt can be sufficiently large for the reflected beams to be reflected in a direction extending away from the pupil of the monitoring beam.

The term "pupil of the monitoring beam" denotes the image of a diaphragm in the optical path of the monitoring beam. The reflected beams thus pass in a direction extending away from the monitoring beam passing to the image sensor so that reflex effects of the lenses are prevented. The invention thus provides an objective in which the reflex effects of the lenses are obviated by arranging the lenses in selectively tilted positions, by which means the resulting aberrations are compensated.

The group of lenses of the objective that is disposed on the object side is also referred to as a field lens. The individual lenses cooperate with each other such that the field lens focuses the monitoring beams onto the plane of the object to be measured.

The objective comprises means to tilt the lenses relatively to the illuminating beam. These means can be holding devices such as holding rings or holding mounts that position the lenses at a defined angle relative to the monitoring beam in a position that is predetermined when designing the objective. In this case, it is advantageous to install the lenses at a defined angle of tilt during assembly thereof.

A dental camera is used intraorally in order to image structures such as teeth or tooth stumps as objects to be measured. The objective of the invention comprises at least two lenses that are tilted relatively to each other. The light source emits an illuminating beam that has a monochromatic or a polychromatic spectrum depending on the measuring method used. The lenses have optical axes that represent symmetry axes passing through the center of the lenses. The lenses are tilted such that reflected beams are reflected by both surfaces of each lens, namely a first surface facing the light source and a second surface remote from the light source, in a direction extending away from the optical path of the monitoring beam, so that there are no disturbing reflex effects resulting from superimposition of the reflected beam and the monitoring beam. The reflected beams thus do not, in particular, impinge on the image sensor so that image interference caused by reflected light is eliminated.

The so-called Koehler illumination, which is primarily used for optical structures in microscopy, can be the type of illumination used.

The purpose of Koehler illumination is to provide the brightest and most uniform illumination as possible on the object to be measured.

The light coming from the light source is focused by a collector lens. The light source itself is imaged by a collector lens in the plane of a so-called aperture diaphragm disposed in a focal plane of the condenser lens. This image of the light source is reproduced by the condenser lens as a uniformly distributed light field on the plane of the object to be measured. By way of the condenser lens, the illuminating beams impinge on the object to be measured as parallel bundles of rays that form a field of illumination of uniformly distributed luminosity.

The objective of the invention is particularly well-suited for the use of the so-called triangulation method for three-dimensional scanning.

A triangulation method is suitable for the optical measurement of three-dimensional geometries of an object to be measured, for which purpose a pattern that can comprise a plurality of parallel stripes of light is projected onto the object to be measured. The projected pattern is recorded in a plurality of images. The three-dimensional geometry of the object to be measured can then be deduced from the resulting profile of the projections of the pattern.

As a result of the reduction of the reflex effect, the image of the object to be measured is not falsified by punctiform brightening.

Furthermore, the objective of the invention does not require an expensive coating on the lens surfaces to reduce reflections. However, additional coating of the lenses may improve the optical properties.

Advantageously, at least one surface of the lenses can have a concave shape with a curvature such that the reflected beam is focused onto a focal point located in the plane of a telecentric diaphragm and away from its aperture.

The concave shape can have a spherical curvature or any other curvature of a shape capable of causing the incident illuminating beams to be reflected such that the reflected beams are focused to the focal point.

The illuminating rays first impinge on the light-source-side concave surface of the first light-source-side lens and then on that side of the first lens that is remote from the light source. The beams reflected by the light-source-side surface are then focused onto a first focal point. The beams reflected by the object-side surface are first refracted at the light-source side surface and focused onto a second focal point. The beams reflected by the light-source side surfaces and those surfaces of the other lenses pertaining to the field lens that are remote from the light source are refracted by the surfaces of the lenses located between them and the light source and are likewise focused to the respective focal points. The different focal points located away from the diaphragm aperture can coincide at a common point or be spaced from each other.

Thus it is sufficient to tilt the lenses to a small extent in order to direct the reflected beams focused onto the respective focal points toward a region located away from the aperture of the telecentric diaphragm. The extent to which the lenses must be tilted depends on the aperture of the imaging system.

Advantageously, a second lens can be tilted relatively to the illuminating beam by an angle of tilt β, the second lens being disposed downstream of the first lens in the direction of the illuminating beam so that the aberrations resulting from the tilted position of the first lens tilted by an angle α are totally or partly compensated by the second lens so as to achieve the desired optical properties of the objective.

The entire optical system comprising the first and second lenses jointly forming the field lens thus functions in the manner of a conventional field lens comprising a single lens or a plurality of parallel lenses and having the desired optical properties. However, the compensation of aberrations may leave a residual compensation error.

Advantageously, the geometric parameters and material characteristics such as radii, types of glass, refractive indices, distances, and angles of tilt of the lenses are chosen such that the aberrations are compensated to a sufficient extent in order to achieve the desired optical properties of the objective.

Thus compensation is optimized to reduce the residual compensation error. The parameters are chosen according to usual selection criteria in order to minimize the optical image defects such as aberrations, coma, astigmatism, distortion, chromatic aberration, scattered light, and absorption.

Advantageously, the choice of the geometric parameters and material characteristics, such as radii, types of glass, refractive indices, distances, and angles of tilt of the lenses, is effected by computer implementing an optimization algorithm.

The parameters for optimum compensation are computed implementing an optimization algorithm such that the residual compensation error is minimized.

Advantageously, the compensation of aberrations can be carried out on pairs of lenses when the objective comprises an even number of lenses.

Thus definition of the individual lens parameters is simplified, since it is then only necessary to consider the parameters of two lenses. Furthermore, the computation of the main lens parameters for compensation of a pair of lenses is less complicated than compensation for a group of three or more lenses.

Advantageously, the first lens disposed on the light-source side can be tilted by an angle α in two planes, namely by a first tilt in a first plane and a second tilt in a second plane.

The reflected beam can thus assume a direction that is at a larger angle relative to the optical path of the monitoring beam and thus reduces the reflex effect. The two planes can, in particular, be at right angles to each other.

Advantageously, the first lens disposed on the light-source side can be tilted about a tilt axis, and the other lenses are tilted about tilt axes that are parallel to the tilt axis of the first lens, which tilt axes are at right angles to the plane of triangulation.

The tilt axes are parallel to each other so that the optical axes of the lenses lie in a plane.

The tilt axes represent axes about which the individual lenses are tilted relatively to the initial position in which the optical axis is parallel to the direction of the illuminating beam.

The process of defining the lens parameters is thus facilitated, since the degrees of freedom of tilt are restricted by the condition requiring that the tilt axes be parallel to each other.

The illuminating beam and the monitoring beam span a plane of triangulation. The tilt axes are at right angles to the plane of triangulation and parallel to each other so that the tilt axes need not lie in a plane and the lenses can be arranged so as to be offset relatively to each other.

Advantageously, a calibration unit can be provided, by means of which a residual compensation error resulting from the optical compensation of the tilted positions of the lenses can be computed, in the form of a systematic error, from the image data produced by the image sensor, implementing a calibration procedure.

Thus the residual compensation error is corrected as a systematic error and the imaging accuracy is improved.

The invention further relates to a method for designing an objective for a dental camera, which objective comprises at least two lenses, and the dental camera comprises a light source and an image sensor, an illuminating beam emerging from the light source being focused by the objective and imaged on an object to be measured and reflected by the object to be measured to form a monitoring beam, which passes through the objective and is directed toward the image sensor, the illuminating beam being partially reflected by a surface of any one of the lenses to form a reflected beam. Each of the lenses is tilted relatively to the illuminating beam such that the optical axis of each lens encloses an angle of tilt with the illuminating beam, which angle of tilt is sufficiently large to cause the reflected beams to assume a direction extending away from the pupil of the monitoring beam.

The method of the invention can be carried out using the objective of the invention.

One advantage of this method is that the lenses need not be finished in conventional manner by an expensive process for the reduction of reflex effects, but instead, the individual lenses are arranged in tilted positions so that the reflected beams assume a direction extending away from the pupil of the monitoring beam and thus do not pass to the image sensor. However, non-tilted coated lenses exhibit fewer reflex effects despite smaller reflections since a small portion of light is reflected. In the case of a coating on the individual lenses, the reflex effects can be almost eliminated.

Advantageously, the geometric parameters and material characteristics, such as radii, types of glass, refractive indices, distances, and angles of tilt of the lenses, can be chosen when designing the objective such that the aberrations are compensated to an extent sufficient to achieve the desired optical properties of the objective.

The choise of the geometric parameters and material characteristics of the lenses when designing the objective is the main factor determining the degree of compensation of imaging defects.

Advantageously, the geometric parameters and material characteristics, such as radii, types of glass, refractive indices, distances, and angles of tilt of the lenses, can be chosen by computer implementing an optimization algorithm.

The time taken to design the objective is thus reduced and the computer-aided choice of the geometric parameters and material characteristics results in a computer-aided optimization of compensation for diminishing the residual compensation error.

Advantageously, a systematic residual compensation error can result during said compensation procedure, which systematic residual compensation error is computed from the image data produced by the image sensor by means of a calibration unit implementing a calibration procedure.

The residual compensation error is thus calibrated and the optical imaging quality is improved.

Advantageously, the optical components disposed upstream and downstream of the objective can be adjusted by computer implementing an optimization algorithm.

If the objective of the invention is used in an existing system comprising additional optical components, the other optical components can be adjusted to match the altered optical properties of the objective of the invention implementing an optimization algorithm.

BRIEF DESCRIPTION OF THE DRAWINGS

Exemplary embodiments of the invention are described with reference to the drawings, in which.

EXEMPLARY EMBODIMENTS

Figure 1:
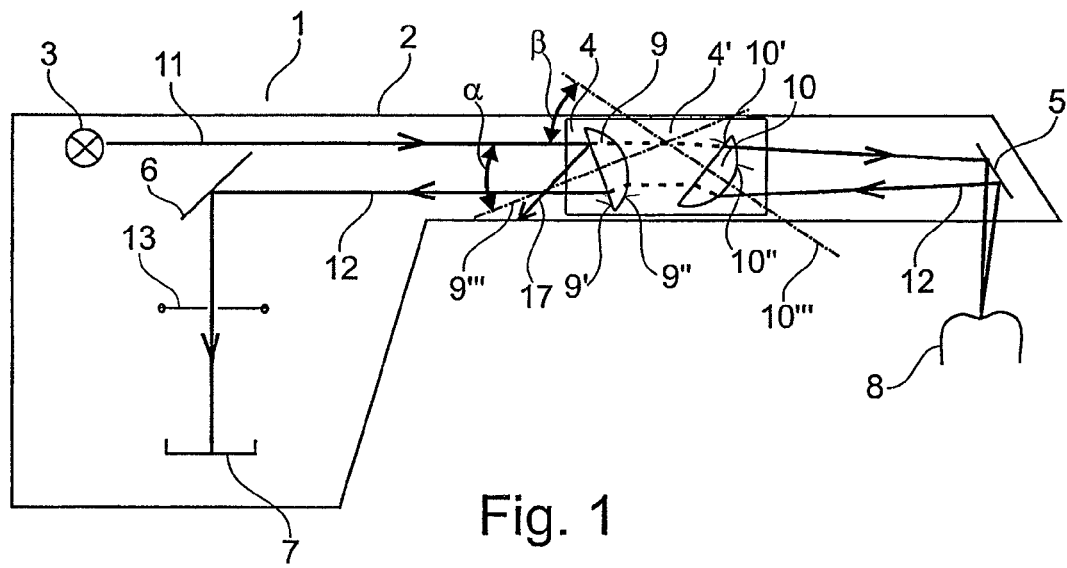
FIG. 1 shows a dental camera comprising the objective of the invention containing two lenses.

FIG. 1 shows a dental camera 1 of the invention comprising a camera housing 2 including a light source 3, an objective 4, a first deflecting mirror 5, a second deflecting mirror 6, and an image sensor 7. The dental camera shown is suitable for intraoral applications for the purpose of imaging intraoral structures such as a tooth shown in the figure as the object 8 to be measured. In the embodiment shown, the objective 4 contains two lenses 9 and 10 that are tilted relatively to one another and are disposed in a predetermined manner in a planned position at an intended angle in the objective 4. The lenses 9 and 10 form a so-called field lens 4'. The light source 3 emits an illuminating beam 11 that is focused by the lenses 9 and 10 within the objective 4, deflected by the first deflecting mirror 5 onto the object to be measured 8, and reflected by the object 8 to be measured to form a monitoring beam 12, and deflected by the first deflecting mirror 5 back to the objective 4 in the form of the monitoring beam 12. The monitoring beam 12 is guided by the objective to the second deflecting mirror 6, and deflected by the second deflecting mirror 6 toward the image sensor 7, which supplies image data for further evaluation.

A telecentric diaphragm 13 is disposed between the second deflecting mirror 6 and the image sensor 7 in the focal plane of the objective 4 so that only the beams traveling through the focal point of the objective 4 are allowed to pass through the telecentric plane. The advantage of this telecentric arrangement is that the size of the image and the depth of focus remain almost constant when the object distance is altered.

A disadvantage of such telecentric optics is the low light intensity of the light signal arriving at the image sensor 7. A prerequisite for the mode of operation of the telecentric objective is that the diameter of the objective has to be at least equal to the size of the object 8 to be measured.

Furthermore, the so-called Koehler illumination, which is primarily used for optical systems in microscopy, is used as the form of illumination.

The Koehler illumination is intended to provide the brightest and most uniform illumination on the object to be measured.

The light from the light source is focused by a collector lens (not shown). The light source itself is imaged by a collector lens in the plane of a so-called aperture diaphragm (not shown) that corresponds to the telecentric diaphragm located in the focal plane of the field lens 4'. The focused image of the light source is thus imaged by the field lens 4' as uniformly distributed light on the plane of the object 8 to be measured. The field of illumination of the illuminating beams 11 thus has uniformly distributed luminosity.

In place of the second deflecting mirror 6, a semitransparent beam splitter can be provided that allows the illuminating beam to pass through, in part, and deflects the monitoring beam 12 toward the image sensor 7. The optical path of the illuminating beam 11 matches that of the monitoring beam 12 between the beam splitter and the object 8 to be measured.

The light source 3 can be a polychromatic or a monochromatic light source depending on the imaging procedure used. The lens 9 has an optical axis 9''' and the lens 10 has an optical axis 10'''. The first lens 9 disposed on the light-source side is tilted by an angle α relatively to the illuminating beam 11 to such an extent that a reflected beam 17 coming from that surface 9' of the first lens 9 that is disposed on the light-source side is reflected in a direction extending away from the optical path of the monitoring beam 12 so that there is no disturbing reflex effect on the image sensor caused by superimposition of the reflected beam 17 on the monitoring beam 12. As a result of this diminishment of the reflex effect, the image contrast is increased and the image is not falsified by punctiform brightening.

The second lens 10 is arranged relatively to the first lens 9 such that aberrations resulting from the tilted position of the first lens 9 are compensated by the second lens 10 as far as possible. As an optical system, the overall objective 4 consisting of the lenses 9 and 10 has the desired optical properties of a conventional objective. These desired optical properties include a correction of defects such as spherical aberration, field curvature, astigmatism, distortion, and chromatic aberration. The radii, types of glass, refractive indices, distances, and angles of tilt of the lenses 9 and 10 are chosen such that the desired optical properties of the objective 4 are achieved. Optimization of these parameters can be achieved by means of an optimization algorithm with the aid of a computer.

An object-side surface 9" of the first lens 9, a light-source-side surface 10', and an object-side surface 10" of the second lens 10 are likewise arranged such that the reflected beams coming from these surfaces do not impinge on the image sensor 7.

The illuminating beam 11 and the monitoring beam 12 span a plane of triangulation 28.

Figure 2:
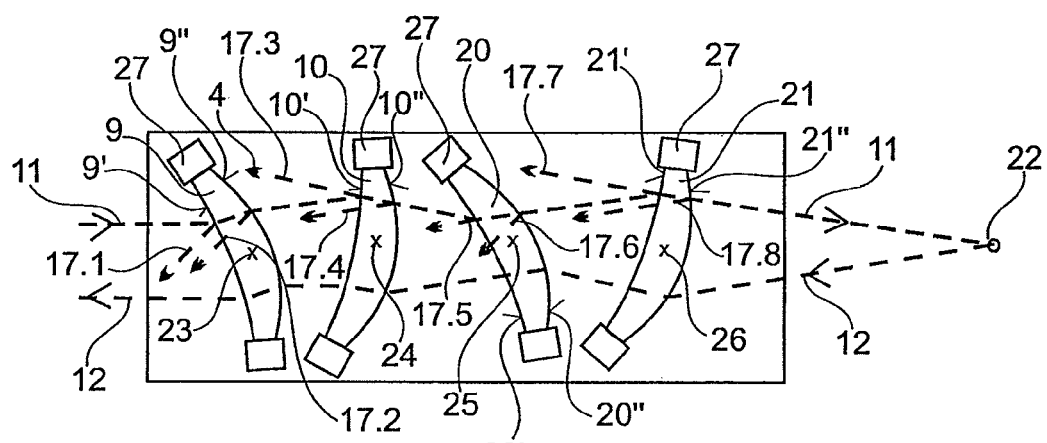
FIG. 2 shows the objective of the invention containing four lenses.

FIG. 2 shows the objective 4 of the dental camera shown in FIG. 1, containing four lenses 9, 10, 20, and 21. The optical path of the illuminating beam 11 and the optical path of the monitoring beam 12 are shown diagrammatically. The compensation of aberrations is carried out in pairs of lenses, so that the aberrations resulting from the tilted position of the first lens 9 are compensated by the tilted position of the second lens 10, and the aberrations resulting from the tilted position of the third lens 20 are compensated by the tilted position of the fourth lens 21. The field lens 4' of the objective 4 has the optical properties of a conventional objective having a punctiform focal point 22. The lenses 9, 10, 20, and 21 are tilted about the tilt axes 23, 24, 25, and 26, the tilt axes 23, 24, 25 and 26 extending parallel to each other and being disposed in a plane so that the optical axes 9''', 10''', 20''' and 21''' of the lenses 9, 10, 20, and 21 are tilted in a plane. The objective 4 can alternatively comprise five or more lenses.

The lenses 9, 10, 20, and 21 are tilted such that the reflected beam 17.1 from the light-source side surface 9', the reflected beam 17.2 from the object-side surface 9'', the reflected beam 17.3 from the light-source side surface 10', the reflected beam 17.4 from the object-side surface 10'', the reflected beam 17.5 from the light-source side surface 20', the reflected beam 17.6 from the object-side surface 20'', the reflected beam 17.7 from the light-source side surface 21', and the reflected beam 17.8 from the object-side surface 21'' are deflected in a direction extending away from the aperture 13.1 of the telecentric diaphragm 13 and thus do not pass to the image sensor 7.

The objective 4 comprises means 27 for holding the lenses 9, 10, 20, and 21, such as holding mounts that ensure that the lenses 9, 10, 20, and 21 are mounted in a manner that is predetermined when designing the desired objective 4.

Figure 3:
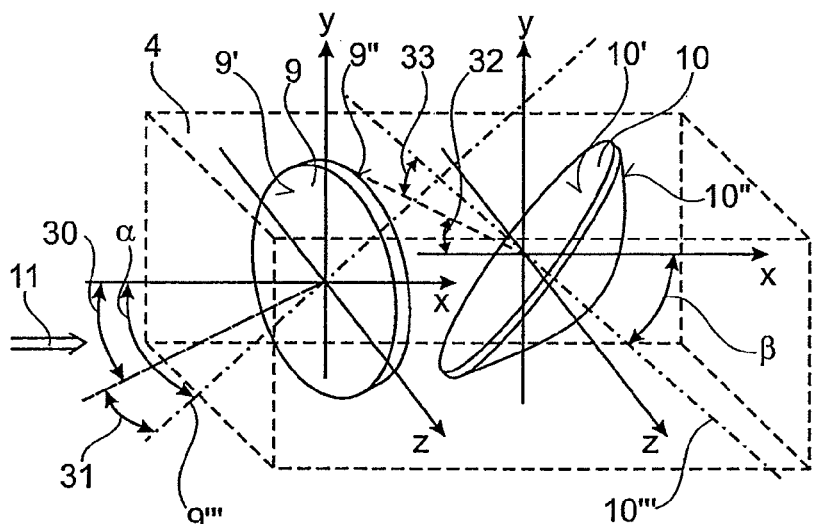
FIG. 3 shows the objective of the invention containing two lenses, in which compensation is carried out in two planes.

FIG. 3 shows the objective 4 of the invention shown in FIG. 1 in a perspective view, the first lens 9 and the second lens 10 being tilted not only in one plane but in two planes. The optical axis 9''' of the lens 9 and the optical axis 10''' of the lens 10 are shown in the form of dot-dash lines. A Cartesian coordinate system comprising the x, y, and z axes has been placed at the center of the lens 9. The lens 9 is tilted by the angle 30 in the x-y plane and additionally by the angle 31 in the x-z plane. The spacing and tilt of the lens 10 are selected such that the aberrations caused by the tilted position of the lens 9 are compensated. A Cartesian coordinate system comprising the x, y, and z axes is likewise placed within the lens 10 at the center thereof. The second lens 10 is tilted by the angle 32 in the x-y plane and additionally by the angle 33 in the x-z plane.

The objective 4 of the invention can also comprise a plurality of lenses that are tilted in two or three planes, each pair of lenses compensating the aberrations resulting from the tilted positions thereof.

The angles α and β of the tilt of the lenses 9, 10 relative to the illuminating beam 11 are chosen such that the reflected beam 17.1 from the light-source side surface 9', the reflected beam 17.2 from the object-side surface 9'', the reflected beam 17.3 from the light-source side surface 10', and the reflected beam 17.4 of the object-side surface 10'' are deflected in a direction extending away from the aperture 13.1 of the telecentric diaphragm 13 shown in FIG. 1 and these reflected beams thus do not travel toward the image sensor 7.

Figure 4:
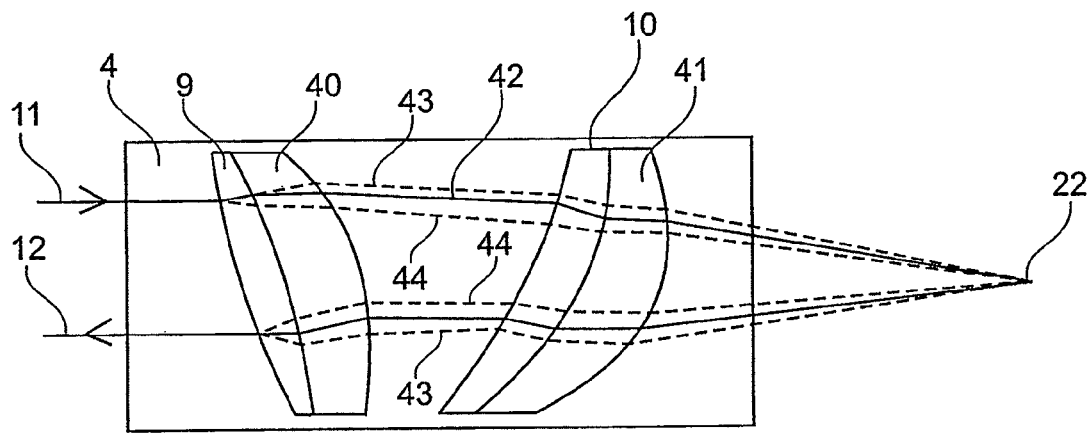
FIG. 4 shows the objective of the invention containing two lenses and two achromatic lenses.

FIG. 4 diagrammatically shows the objective 4 of the invention shown in FIG. 1 comprising a first lens 9 and a second lens 10, an additional lens 40, and 41 of the same size being further attached to each lens and the optical system comprising the lenses 9, 40, 10, and 41 forms an achromatic lens. In optics, the term "achromatic lens" is understood to mean a system comprising a plurality of lenses that have the same size and that are made of types of glass of different Abbe coefficients. The result of using an achromatic lens is that the imaging defect of chromatic aberration is corrected. An achromatic lens comprising two lenses can correct the chromatic aberration for two wavelengths, the shape of the lenses and the ratio of Abbe coefficients being selected such that the focal points of the light beams of both wavelengths coincide. In the case of an achromatic lens comprising three lenses, it is possible to compensate the chromatic aberration for three wavelengths.

Furthermore, the aperture aberration (spherical aberration) can be minimized by a suitable choice of geometry and materials. Achromatic lenses are thus also highly suitable in monochromatic applications for optimum focusing. Achromatic lenses also permit the correction of coma in the paraxial region. This type of correction ensures an insensitivity of the optical system to small angles of tilt. Small and wide objects can therefore be imaged properly.

In the present case, the chromatic aberration of the objective 4 is compensated for red and blue light. The continuous line shows the optical path of the green light beam 42, a dashed line shows the optical path of the blue light 43, and the second dashed line shows the optical path of the red light 44. The illuminating beam 11 and monitoring beam 12 are shown. The optical paths of the blue light 43, green light 42 and the red light 44 have the same focal point 22 so that the chromatic aberration for the wavelengths of the blue, green, and red light is compensated.

Figure 5:
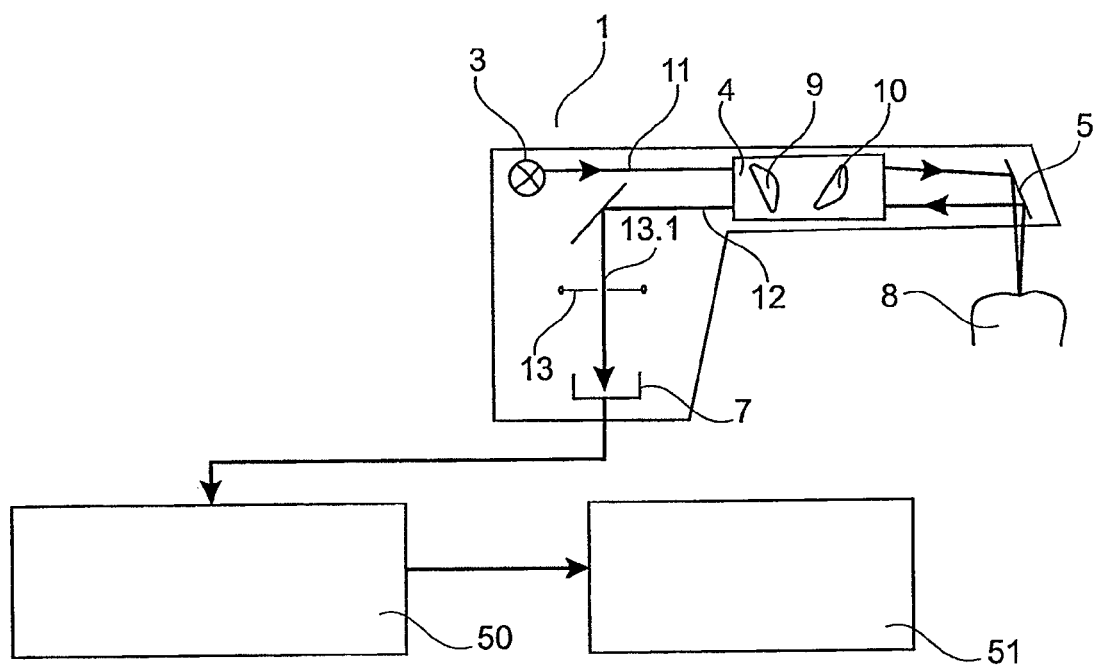
FIG. 5 is a diagram illustrating the calibration procedure.

FIG. 5 is a diagram illustrating the calibration of a residual compensation error that results during the compensation of aberrations in the objective 4 of the invention. The radii, types of glass, refraction indices, distances, and angles of tilt α, β of the lenses 9 and 10 are chosen such that the aberrations caused by the tilted position of the first lens 9 are almost completely compensated. The choice of these factors can be carried out by computer implementing an optimization algorithm. However, complete compensation cannot be achieved in practice so that a residual compensation error leads to an imaging defect. This residual compensation error can be calibrated by means of a calibration unit 50 and subtracted in the form of a systematic error from the image data of the image sensor 7. The corrected image data are then transferred to an evaluation unit 51 for further analysis of the image.

Figure 6:
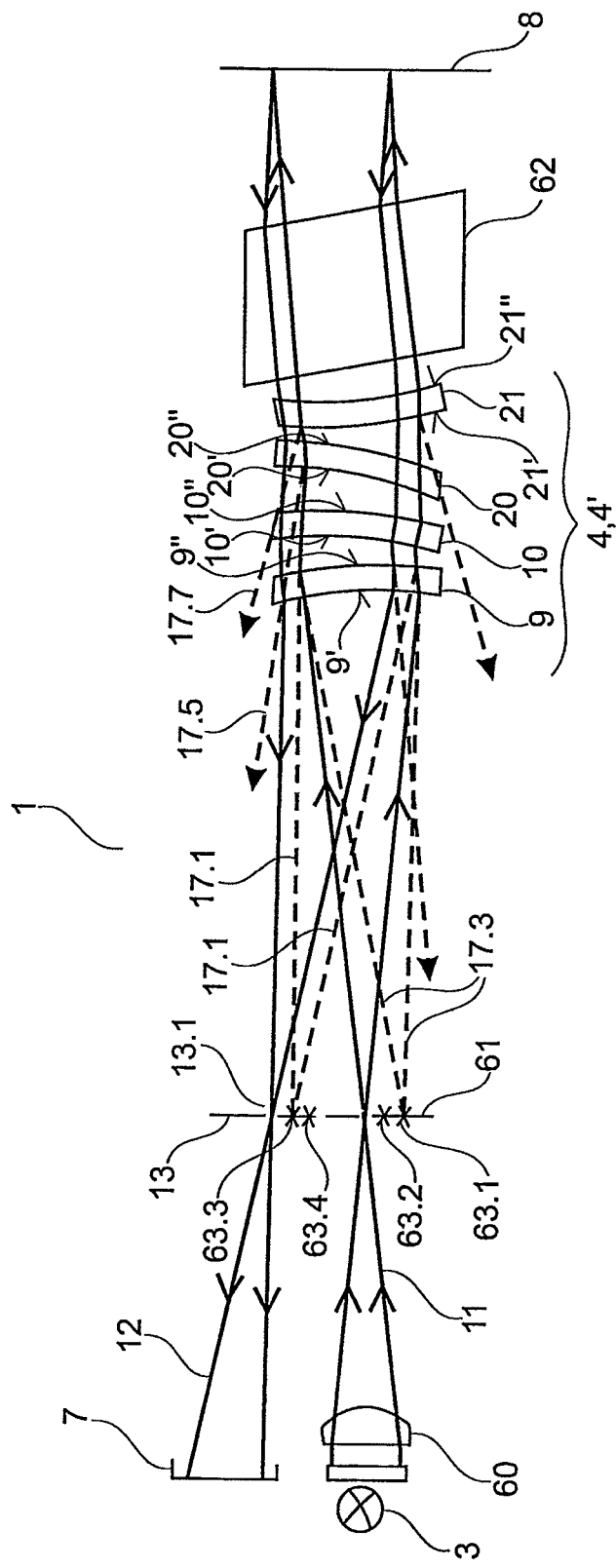
FIG. 6 shows an alternative embodiment of the dental camera comprising the objective of the invention.

FIG. 6 shows an alternative embodiment of the dental camera 1 comprising a light source 3, an objective 4, and an image sensor 7. The light source 3 emits an illuminating beam 11 that is focused by a collector lens 60. The light source 7 itself is imaged by the collector lens 60 in the plane of an aperture diaphragm 61 located in the focal plane of the field lens 4' comprising the lenses 9, 10, 20, 21. The focused image of the light source is imaged by the field lens 4' in the form of uniformly distributed light on the plane of the object 8 to be measured. The illumination field of the illuminating beams 11 thus has uniformly distributed luminosity, the illuminating beams 11 being incident on the plane of the object 8 to be measured such that they are focused parallel to each other. This type of illumination is referred to as Koehler illumination.

A prism 62 that aligns the illuminating beams 11 is disposed between the field lens 4' and the surface of the object 8 to be measured. The illuminating beams 11 impinge on the surface of the object 8 to be measured and are reflected in the form of monitoring beams 12. The monitoring beams 12 are focused by the prism 62 and the lenses 9, 10, 20, 21 and focused onto the opening of the telecentric diaphragm 13, and the monitoring beams pass toward the image sensor 7.

The aperture diaphragm 61 and the telecentric diaphragm 13 are disposed in the same plane.

The light-source side surface 9' and the object-side surface 9" of the first lens 9 and the light-source side surface 10' and the object-side surface 10" of the second lens 10 have a concave curvature such that the reflected beam 17.1 is focused onto a first focal point 63.1, the reflected beam 17.2 is focused onto a second focal point 63.2, the reflected beam 17.3 is focused onto a third focal point 63.3, and the reflected beam 17.4 is focused onto a fourth focal point 63.4. All of the focal points 63.1 to 63.4 are disposed in the plane of the telecentric diaphragm 13 away from the aperture 13.1 of the telecentric diaphragm 13. The surfaces 20', 20", 21', 21" of the other lenses 20, 21 do not have a concave curvature, but they are tilted such that the reflected beams 17.5 to 17.8 are reflected in a direction extending away from the aperture 13.1 of the telecentric diaphragm 13.

The invention claimed is:

1. An objective for use in a dental camera that includes a light source, an image sensor, and a telecentric diaphragm, the objective comprising:
   at least two lenses including a first lens and a second lens; and
   a holding unit arranged to hold the at least two lenses such that: (i) an illuminating beam received on a light source side of the objective is guided by the at least two lenses and emanated from an object side of the objective, and (ii) a monitoring beam, formed by a reflection of the illuminating beam from an object to be measured and received from the object side of the objective, is guided by the at least two lenses and emanated from the light source side of the objective towards an aperture of a telecentric diaphragm and onto the image sensor,
   wherein the holding unit is arranged to hold the first lens such that an optical axis of the first lens forms a first angle of tilt with respect to the illuminating beam so that a reflected beam from a concave light source side surface of the first lens is reflected in a direction extending away from the aperture of the telecentric diaphragm, and
   wherein the holding unit is arranged to hold the second lens of the at least two lenses such that an optical axis of the second lens forms a second angle of tilt with respect to the illuminating beam to correct for aberrations caused by the tilt of the first lens at the first angle.

2. The objective as defined in claim 1, wherein the holding unit is further arranged to hold the first lens at the first angle of tilt such that the reflected beam from the concave light source side surface of the first lens does not impinge on the image sensor.

3. The objective as defined in claim 1, wherein the second lens is located on an object side of the first lens.

4. The objective as defined in claim 1, wherein geometrical parameters and material characteristics, including radii, types of glass, and refractive indices of the at least two lenses, and relative distances between the at least two lenses, are such that the aberrations are compensated.

5. The objective as defined in claim 4, wherein the geometrical parameters and the material characteristics of the objective were determined according to an optimization algorithm.

6. The objective as defined in claim 3, wherein, if a quantity of the at least two lenses is an even number, aberrations are compensated using pairs of the at least two lenses.

7. The objective as defined in claim 1, wherein the at least two lenses are each tilted in a first plane and a second plane, the first plane being perpendicular to the second plane.

8. The objective as defined in claim 3, wherein the first lens is tilted towards the light source side of the objective at the first angle of tilt about a tilt axis, and one or more other of the at least two lenses are tilted about tilt axes that are parallel to the tilt axis of the first lens, the tilt axes being perpendicular to a triangulation plane formed between the illuminating beam and the monitoring beam.

9. A dental camera system, comprising:
   the objective recited in claim 3; and
   a calibration unit constructed to compute a systematic residual compensation error using image data generated by the image sensor.

10. The objective as defined in claim 1, wherein the holding unit is further configured to tilt one of the at least two lenses in another plane.

11. The objective as defined in claim 10, wherein the holding unit is further configured to tilt one of the at least two lenses in a third plane.

12. The objective as defined in claim 1, wherein a first additional lens is attached to an object side surface of the first lens and a second additional lens is attached to an object side surface of the second lens.

13. A method of using an objective in a dental camera that includes a light source, an image sensor, and a telecentric diaphragm, the method comprising:
   guiding an illuminating beam emitted by the light source and received on a light source side of the objective using at least two lenses of the objective, including a first lens and a second lens, such that the illuminating beam emanates from an object side of the objective and onto an object to be measured;
   receiving a monitoring beam on the object side of the objective, the monitoring beam being formed by a reflection of the illuminating beam from the object to be measured; and
   guiding the monitoring beam using the at least two lenses through the objective such that the monitoring beam emanates from the light source side of the objective towards an aperture of a telecentric diaphragm and onto the image sensor,
   wherein the first lens is oriented such that an optical axis of the first lens forms a first angle of tilt with respect to the illuminating beam so that a reflected beam from a concave light source side surface of the first lens is reflected in a direction extending away from the aperture of the telecentric diaphragm, and
   wherein the second lens of the at least two lenses is oriented such that an optical axis of the second lens forms a second angle of tilt with respect to the illuminating beam to correct for aberrations caused by the tilt of the first lens at the first angle.

14. The method as defined in claim 13, wherein geometrical parameters and material characteristics, including radii, types of glass, and refractive indices of the at least two lenses, and relative distances between the at least two lenses are such that aberrations are compensated.

15. The method as defined in claim 14, wherein the geometrical parameters and the material characteristics of the objective were determined according to an optimization algorithm.

16. The method as defined in claim 14, further comprising:
   computing a systematic residual compensation error caused by the objective from image data generated by the image sensor.

17. The method as defined in claim 13, wherein optical components of the objective were adjusted by a computer performing an optimization algorithm.

18. The method as defined in claim 13, wherein the first lens is oriented at the first angle of tilt such that the reflected beam from the concave light source side surface of the first lens does not impinge on the image sensor.

19. The method as defined in claim 13, wherein one of the at least two lenses is tilted in another plane.

20. The objective as defined in claim 19, wherein one of the at least two lenses is tilted in a third plane.

* * * * *